(12) United States Patent
Ichim et al.

(10) Patent No.: US 11,266,707 B2
(45) Date of Patent: Mar. 8, 2022

(54) NUTRACEUTICALS FOR THE PREVENTION, INHIBITION, AND TREATMENT OF SARS-COV-2 AND ASSOCIATED COVID-19

(71) Applicants: Thomas E Ichim, Oceanside, CA (US); Timothy G Dixon, Oceanside, CA (US)

(72) Inventors: Thomas E Ichim, Oceanside, CA (US); Timothy G Dixon, Oceanside, CA (US)

(73) Assignee: Therapeutic Solutions International, Inc., Oceanside, CA (US)

( * ) Notice: Subject to any disclaimer, the term of this patent is extended or adjusted under 35 U.S.C. 154(b) by 0 days.

(21) Appl. No.: 16/866,430

(22) Filed: May 4, 2020

(65) Prior Publication Data

US 2021/0338763 A1    Nov. 4, 2021

(51) Int. Cl.

| | |
|---|---|
| *A61K 36/82* | (2006.01) |
| *A61K 36/45* | (2006.01) |
| *A61K 36/71* | (2006.01) |
| *A61K 31/26* | (2006.01) |
| *A61K 31/353* | (2006.01) |
| *A61K 31/09* | (2006.01) |
| *A61K 31/122* | (2006.01) |
| *A61K 36/31* | (2006.01) |

(52) U.S. Cl.
CPC .............. *A61K 36/82* (2013.01); *A61K 31/09* (2013.01); *A61K 31/122* (2013.01); *A61K 31/26* (2013.01); *A61K 31/353* (2013.01); *A61K 36/31* (2013.01); *A61K 36/45* (2013.01); *A61K 36/71* (2013.01)

(58) Field of Classification Search
CPC .. A61K 2300/00; A61K 31/09; A61K 31/122; A61K 31/26; A61K 31/353; A61K 36/31; A61K 36/45; A61K 36/71; A61K 36/82
See application file for complete search history.

(56) References Cited

U.S. PATENT DOCUMENTS 8,153,166 B2 *   4/2012   Lin .......................... A61P 43/00
                                                          424/725

\* cited by examiner

*Primary Examiner* — Aaron J Kosar

(74) *Attorney, Agent, or Firm* — Baumgartner Patent Law; Marc Baumgartner

(57) ABSTRACT

Disclosed herein are methods of treating or preventing complications associated with a SARS-CoV-2 infection, comprising: administration of a combination comprising: a) Green Tea and/or extract thereof; b) Blueberry and/or extract thereof; c) *Nigella sativa* and/or extract thereof; and d) broccoli and/or extract thereof in an amount and frequency sufficient to treat or prevent complications associated with said SARS-CoV-2 infection.

16 Claims, No Drawings

NUTRACEUTICALS FOR THE PREVENTION, INHIBITION, AND TREATMENT OF SARS-COV-2 AND ASSOCIATED COVID-19

FIELD OF THE INVENTION

The invention relates to the field of viral infections, more specifically, the invention pertains to treatment of viral infections using nutraceutical interventions.

BACKGROUND

SARS-CoV-2, the viral pathogen causative of COVID-19, is a novel coronavirus that is most phylogenetically similar to SARS. The virus is presumed to have initially been transmitted from an animal reservoir (bats) to humans, most likely via an amplifying host (pangolin) [1, 2]. It is a single strand positive sense RNA virus whose infectivity is mediated by the envelope spike (S) glycoprotein which binds to its cellular receptor angiotensin-converting enzyme 2 (ACE2) [3]. Interestingly, antibody responses have also been detected towards the S glycoprotein [3-6].

It is known that Coronaviruses (CoVs) belong to a subfamily of large and enveloped viruses containing a single strand of sense RNA. There are four genera, of CoVs, i.e., alpha, beta, gamma, and delta, of which alpha- and beta-CoVs are known to infect humans [7]. Infectivity of CoVs is mediated by the envelope spike (S) glycoprotein which binds to its cellular receptors angiotensin-converting enzyme 2 (ACE2) and dipeptidyl peptidase 4 (DPP4) for SARS-CoV and MERS-CoV, respectively, this facilitates fusion of the virus with the membrane [8, 9]. The viral RNA genome is released into the cytoplasm; after replication of the viral genome, genomic RNA accompanied by envelope glycoproteins and nucleocapsid proteins forms virion-containing vesicles, which then fuse with the plasma membrane to release the virus [10]. The viral cause of COVID-19 is attributed to the SARS-CoV-2 type of CoV, which was found to be a new type of beta-CoV with more than 99.98% genetic identity among 10 sequenced samples collected from the original site of the outbreak [11]. SARS-CoV-2 is genetically more similar to SARS-CoV than to MERS-CoV [12].

Subsequent to the virus binding to the target cells, which appear to be primarily type 2 pulmonary epithelial cells, the virus fuses with the cellular membrane, allowing viral entry into the cytoplasm [13]. Once the viral genome is unleashed in the cell, it replicates and the viral RNA accompanied by envelope glycoproteins and nucleocapsid proteins form virion-containing vesicles, which then fuse with the plasma membrane to release the virus [14].

At a clinical level, the usual presentation of COVID-19 is pneumonia, as demonstrated by computer tomographic (CT) scan or chest X-ray and fever. At the beginning phases of the infection, the patients showed the acute respiratory infection symptoms, with some that quickly developed acute respiratory failure (ARDS) and other serious complications [15]. The original patients that were published from the China Novel Coronavirus Investigating and Research Team all developed severe pneumonia and two of these three patients with available clinical profiles showed a common feature of fever and cough [13].

After this, another study of a family of six patients in the University of Hong Kong-Shenzhen Hospital demonstrated that all of them had pulmonary infiltrates, and other flu-like characteristics [16]. The chest X-ray and CT imaging in a study showed that 75% of 99 patients possessed bilateral pneumonia and the remaining 25% unilateral pneumonia [17]. In total about, 14% of the patients showed multiple mottling and ground-glass opacity [17]. The first cases of coronavirus infection in the United States also showed basilar streaky opacities in both lungs by chest radiography. However, the pneumonia for this patient was only detected on the day 10 of his illness[18].

As reviewed by Zheng [1], identifiable characteristics of COVID19 patients are fever and cough, with fatigue in 96% of patients (n=138) in one study, but was less outstanding (18%, n=44) in another report. Overall analysis revealed that fever was observed in around 90% whereas cough is relatively less at 68%, and shortness of breath, muscle ache, headache, chest pain, diarrhea, haemoptysis, sputum production, rhinorrhoea, nausea and vomiting, sore throat, confusion, and anorexia were also observed in an numerous patients.

Currently no interventions have demonstrated efficacy in double blind trials, however multiple approaches are in development. These can be categorized into a) antigen specific vaccines [19-22]; b) innate immune stimulators [23-25]; c) small molecule antivirals; d) small molecules which modulate viral interactions with host cells [26-29]; e) plasma/antibodies from patients who recovered [30-40]; f) small molecule blockers of cytokine signaling [41-44]; g) antibodies to inflammatory cytokines [45-53]; and h) cell based therapies [54-64].

At present there appears to be no clear consensus on which approaches are most promising, with various institutions utilizing differing protocols. It is expected that clinically significant signals will be reported in up to 18 months from now. In the absence of established pharmaceutical approaches, exploration of scientific based natural based treatments may have merit.

DESCRIPTION OF THE INVENTION

The formulation was based on the desire to develop a multi-angled nutraceutical solution which addressed various aspects of COVID-19. For example, in the beginning of the disease process, the body's susceptibility to infection with the SARS-CoV-2 virus is a major determining factor as to progression of disease. Belonging to the coronavirus family of viruses, it is well recognized that natural killer cells, and interferon responses play a role in host susceptibility. For example, in an early mouse studies it was demonstrated that interferon response negatively correlated with viral susceptibility [65, 66]. In other murine studies it has been demonstrated that successful infection with coronavirus involves viral suppression of the natural kill cell response [67]. Interestingly, agents which increase NK activity has been shown to decrease coronavirus infections. For example, in one study, a novel CpG oligonucleotide (BW001) was assessed, which displays B-type CpG ODN structure feature at the 5' and A-type CpG ODN structure feature at the 3', and tested for its anti-SARS-CoV activity. We found that the supernatants of human PBMCs stimulated by BW001 significantly protected Vero cells from SARS-CoV infection. BW001 could stimulate human PBMCs and pDCs to secrete high level of IFN-alpha and promote human PBMCs and B cells to proliferate. Furthermore, we demonstrated that BW001 could activate CD19+ B cells and CD56+ NK cells in human PBMCs. In addition, BW001 could enhance NK cytotoxicity and IFN-gamma secretion in human PBMCs [68].

Therefore, while there is rationale for stimulation of immunity at the beginning phases of infection, as infection progresses, various types of immunity may be detrimental. For example, it is known that pulmonary inflammation and progression of acute respiratory distress syndrome (ARDS) occurs as a result of excessive immune response. Mortality from COVID-19 is caused by acute respiratory distress syndrome (ARDS) [69, 70], which is caused by unrestrained cytokine release, also known as "cytokine storm", and is characterized by fluid leakage, diffuse inflammation, and disseminated intravascular coagulation, all of which cause impaired alveolar gas exchange. Approximately 35-45% of patients with ARDS will die [71].

The role of inflammatory cytokines in the progression of ARDS and its pathology may be seen in several situations. For example, tumor necrosis factor (TNF)-alpha, has been demonstrated to correlate with severity of ARDS in several studies. In one study, measure plasma TNF alpha levels (pl-TNF alpha) in 34 patients with ARDS and in 16 controls was examined. Plasma, TNF alpha was elevated in 76% of the patients with ARDS (71+/−104 pg/ml) and in 48% of the at-risk patients (47+/−73 pg/ml), providing some indication that TNF-alpha may correlated with ARDS [72]. In another study assessment of TNF-alpha was performed in fourteen hospitalized patients with a diagnosis of SARS-associated coronavirus infection. All patients had fever, dry cough and dyspnea. Twelve were intubated during hospitalization. The median duration from onset of fever to the nadir level or most severe condition was 9 days for hypoxia. The 8 patients who died possessed significantly higher peak levels of serum TNF-alpha compared to those who survived (14 vs 9.1 pg/mL; p=0.06) [73]. Another study demonstrated correlation between TNF-alpha and mortality. The study examined ICU patients on ventilator with (n=9) and without (n=12) evidence of ARDS. The median peak TNF concentration in control patients was 40 ng/L (range less than 40-100 ng/L) and in ARDS patients 231 ng/L (range 100-2550 ng/L; p less than 0.001). All of the control patients were discharged alive from the ICU, whereas 6 of 9 ARDS patients died in the ICU. In 6 ARDS patients, it was possible to measure more than 4 consecutive plasma TNF levels. Of these 6 patients, the 3 with persistent elevations in systemic TNF above 230 ng/L succumbed (p less than 0.05, one-tailed) [74].

It is believed the TNF-alpha production causes pathology in ARDS at several levels. In one experiment, TNF-alpha was administered intratracheally at 500 ng in healthy rats. It was observed that within 5 hours, lung lavage neutrophils, lung myeloperoxidase (MPO) activity, and lung leak was substantially higher in the treated as compared to saline-treated control rats [75]. In another study, it was shown that TNF-alpha maintains viability of neutrophils, thus allowing them to produce exaggerated inflammation responses. Scientists exposed neutrophils TNFalpha (100 ng/mL) in the presence or absence of antibodies to IL-8, and the extent of apoptosis was assessed. An enzyme-linked immunoassay was used to measure levels of the anti-apoptotic cytokine IL-8, induced by TNFalpha-stimulation. Because TNFalpha may mediate its effect through various cell-signaling pathways, the study next assessed the effect of kinase inhibition on the ability of TNFalpha to effect apoptosis and IL-8 production. Treatment with TNFalpha had a biphasic effect: at 4-8 h, apoptosis was increased but was markedly suppressed at 24 h (P<0.05). PMN cultured for 24 h with TNFalpha also showed markedly increased levels of IL-8. Neutralization of IL-8 inhibited the ability of TNFalpha to suppress apoptosis (P<0.05). These data illustrate a novel mechanism by which TNFalpha can indirectly elicit an anti-apoptotic effect via release of the anti-apoptotic chemokine IL-8 [76].

Perhaps one of the most tantalizing supporting evidences that TNF-alpha is a potential cause of ARDS are studies in which TNF-alpha was administered systemically as a cancer therapeutic and one of the adverse effects observed in some patients was a ARDS-type pathology [77].

Another cytokine which has been studied extensively in ARDS is interleukin-6. This cytokine is known to possess pro-inflammatory properties [78], as well as to suppress generation of T regulatory cells and promote Th17 cells [79-81]. It is accepted that in ARDS there is a reduction in T regulatory cells [82], whose role is tissue protection [83], and Th1 7 cells, which are commonly associated with inflammation [84]. In one study, 27 consecutive patients with severe medical ARDS. Plasma levels of tumor necrosis factor alpha (TNF-alpha) and interleukins (ILs) 1 beta, 2, 4, 6, and 8 were measured (enzyme-linked immunosorbent assay [ELISA] method) on days 1, 2, 3, 5, 7, 10, and 12 of ARDS and every third day thereafter while patients were receiving mechanical ventilation. Subgroups of patients were identified based on outcome, cause of ARDS, presence or absence of sepsis, shock, and MODS at the time ARDS developed. Subgroups were compared for levels of plasma inflammatory cytokines on day 1 of ARDS and over time. Of the 27 patients, 13 survived ICU admission and 14 died (a mortality rate of 52%). Overall mortality was higher in patients with sepsis (86 vs 38%, p<0.02). The mean initial plasma levels of TNF-alpha, IL-1 beta, IL-6, and IL-8 were significantly higher in nonsurvivors (p<0.0001) and in those patients with sepsis (p<0.0001). Plasma levels of IL-1 beta (p<0.01) and IL-6 (p=0.03) were more strongly associated with patient outcome than cause of ARDS (p=0.8), lung injury score (LIS), APACHE II score, sepsis (p=0.16), shock, or MODS score. Plasma levels of TNF-alpha, IL-1 beta, IL-6, and IL-8 remained significantly elevated over time (p<0.0001) in those who died. This study strongly supports the addition of IL-6 as another cytokine mediatory involved in the pathogenesis of ARDS [85].

A subsequent study examined 24 ARDS patients with MODS (ARDS+MODS group), 18 patients with ARDS but without MODS (ARDS group), and 55 patients with MODS but without ARDS as controls (control group). It was found that serum IL-6 levels in the ARDS+MODS group were significantly higher than those in the ARDS and MODS groups (P<0.01). The IL-6 levels increased with elevated ARDS illness severity (P<0.01); the sensitivity of IL-6 was high in all groups. Moreover, the IL-6 values were closely associated with patient survival [86]. Several other studies have shown correlation between IL-6 elevation and poor prognosis in ARDS [87-89].

Pterostilbene

Pterostilbene (trans-3,5-dimethoxy-4-hydroxystilbene) is a natural polyphenolic compound, primarily found in fruits, such as blueberries, grapes, and tree wood. It has been demonstrated to possess potent antioxidant and anti-inflammatory properties. It is a dimethylated analog of resveratrol which is found in blueberries [90], and is believed to be one of the active ingredients in ancient Indian Medicine [91]. The pterostilbene molecule is structurally similar to resveratrol, the antioxidant found in red wine that has comparable anti-inflammatory, and anticarcinogenic properties; however, pterostilbene exhibits increased bioavailability due to the presence of two methoxy groups which cause it to exhibit increased lipophilic and oral absorption [92-96]. In animal studies, pterostilbene was shown to have 80% bioavailability compared to 20% for resveratrol making it potentially advantageous as a therapeutic agent [92].

We have demonstrated the pterostilbene administered in the form of nanostilbene in cancer patients results in increased NK cell activity, as well as interferon gamma production. Additionally, pterostilbene has shown to inhibit inflammatory cytokines associated with ARDS. For example, studies have demonstrated inhibition of interleukin-I [97], interleukin-6 [98, 99], interleukin-8 [100], and TNF-alpha [101], by pterostilbene.

COVID-19 has been associated with endothelial activation and coagulopathy. It is interesting to note that numerous studies have demonstrated endothelial protective effects of pterostilbene. For example, Zhang et al. investigated the anti-apoptotic effects of pterostilbene in vitro and in vivo in mice. Exposure of human umbilical vein VECs (HUVECs) to oxLDL (200 μg/ml) induced cell shrinkage, chromatin condensation, nuclear fragmentation, and cell apoptosis, but pterostilbene protected against such injuries. In addition, PT injection strongly decreased the number of TUNEL-positive cells in the endothelium of atherosclerotic plaque from apoE(−/−) mice. OxLDL increased reactive oxygen species (ROS) levels, NF-KB activation, p53 accumulation, apoptotic protein levels and caspases-9 and -3 activities and decreased mitochondrial membrane potential (MMP) and cytochrome c release in HUVECs. These alterations were attenuated by pretreatment. Pterostilbene inhibited the expression of lectin-like oxLDL receptor-I (LOX-1) expression in vitro and in vivo. Cotreatment with PT and siRNA of LOX-1 synergistically reduced oxLDL-induced apoptosis in HUVECs. Overexpression of LOX-1 attenuated the protection by pterostilbene and suppressed the effects of pterostilbene on oxLDL-induced oxidative stress. Pterostilbene may protect HUVECs against oxLDL-induced apoptosis by downregulating LOX-I-mediated activation through a pathway involving oxidative stress, p53, mitochondria, cytochrome c and caspase protease [102]. Endothelial protection by pterostilbene [103, 104], and its analogue resveratrol are well known [105, 106].

Kalonji

First. Taking Kalonji increases the potency of the immune system [107, 108]. Specifically, it has been shown that kalonji activates the natural killer cells of the immune system. Natural killer cells, also called NK cells are the body's first line of protection against viruses. It is well known that patients who have low levels of NK cells are very susceptible to viral infections. Kalonji has been demonstrated to increase NK cell activity. In a study published by Dr. Majdalawieh from the American University of Sharjah, Sharjah, United Arab Emirates [109], it was shown that the aqueous extract of Nigella sativa significantly enhances NK cytotoxic activity. According to the authors, this supports the idea that NK cell activation by Kalonji can protect not only against viruses, but may also explain why some people report this herb has activity against cancer. It is known that NK cells kill virus infected cells but also kill cancer cells. There are several publications that show that Kalonji has effects against cancer [110-124].

Second. Kalonji suppresses viruses from multiplying. If the virus manages to sneak past the immune system and enters the body, studies have shown that Kalonji, and its active ingredients such as thymoquinone, are able to directly stop viruses, such as coronaviruses and others from multiplying. For example, a study published from University of Gaziantep, in Turkey demonstrated that administration of Kalonji extract to cells infected with coronavirus resulted in suppression of coronavirus multiplication and reduction of pathological protein production [125]. Antiviral activity of Kalonji was demonstrated in other studies, for example, for example, viral hepatitis, and others [126].

Third. Kalonji protects the lungs from pathology. Kalonji was also reported by scholars to possess potent anti-inflammatory effects where its active ingredient thymoquinone suppressed effectively the lipopolysaccharide-induced inflammatory reactions and reduced significantly the concentration of nitric oxide, a marker of inflammation [127]. Moreover, Kalonji has been proven to suppress the pathological processes through blocking the activities of IL-1, IL-6, nuclear factor-KB [128], IL-1 P, cyclooxygenase-1, prostaglandin-E2, prostaglandin-D2 [129], cyclocoxygenase-2, and TNF-a [130] that act as potent inflammatory mediators and were reported to play a major role in the pathogenesis of Coronavirus infection.

Fourth. Kalonji protects against sepsis/too much inflammation. In peer reviewed study from King Saud University, Riyadh, Saudi Arabia, scientists examined two sets of mice (n=12 per group), with parallel control groups, were acutely treated with thymoquinone (ingredient from Kalonji) intraperitoneal injections of 1.0 and 2.0 mg/kg body weight, and were subsequently challenged with endotoxin Gram-negative bacteria (LPS O 11 1:B4). In another set of experiments, thymoquinone was administered at doses of 0.75 and 1.0 mg/kg/day for three consecutive days prior to sepsis induction with live Escherichia coli. Survival of various groups was computed, and renal, hepatic and sepsis markers were quantified. Thymoquinone reduced mortality by 80-90% and improved both renal and hepatic biomarker profiles. The concentrations of IL-1a with 0.75 mg/kg thymoquinone dose was 310.8±70.93 and 428.3±71.32 pg/ml in the 1 mg/kg group as opposed to controls (1187.0±278.64 pg/ml; P<0.05). Likewise, IL-10 levels decreased significantly with 0.75 mg/kg thymoquinone treatment compared to controls (2885.0±553.98 vs. 5505.2±333.96 pg/ml; P<0.01). Mice treated with thymoquinone also exhibited relatively lower levels of TNF-a and IL-2 (P values=0.1817 and 0.0851, respectively). This study gives strength to the potential clinical relevance of thymoquinone in sepsis-related morbidity and mortality reduction and suggests that human studies should be performed [131].

Sulforaphane

Sulforaphane [1-isothiocyanato-4-(methylsulfinyl)-butane], an isothiocyanate, is a chemopreventive photochemical which is a potent inducer of phase II enzyme involved in the detoxification of xenobiotics [132]. Sulforaphane is produced from the hydrolysis of glucoraphanin, the most abundant glucosinolate found in broccoli, and also present in other Brassicaceae [133]. Numerous studies have reported prevention of cancer [134-138], as well as cancer inhibitory properties of sulforaphane [139-144]. Importantly, this led to studies which demonstrated anti-inflammatory effects of this compound.

One of the fundamental features of inflammation is production of TNF-alpha from monocytic lineage cells. Numerous studies have shown that sulforaphane is capable of suppressing this fundamental initiator of inflammation, in part through blocking NF-kappa B translocation. For example, Lin et al. compared the anti-inflammatory effect of sulforaphane on LPS-stimulated inflammation in primary peritoneal macrophages derived from Nrf2 (+/+) and Nrf2 (−/−) mice. Pretreatment with sulforaphane in Nrf2 (+/+) primary peritoneal macrophages potently inhibited LPS-stimulated mRNA expression, protein expression and production of TNF-alpha, IL-1beta, COX-2 and iNOS. HO-1 expression was significantly augmented in LPS-stimulated Nrf2 (+/+) primary peritoneal macrophages by sulforaphane.

Interestingly, the anti-inflammatory effect was attenuated in Nrf2 (−/−) primary peritoneal macrophages. We concluded that SFN exerts its anti-inflammatory activity mainly via activation of Nrf2 in mouse peritoneal macrophages [145]. In a similar study, LPS-challenged macrophages were observed for cytokine production with or without sulforaphane pretreatment. Macrophages were pre-incubated for 6 h with a wide range of concentrations of SFN (0 to 50 µM), and then treated with LPS for 24 h. Nitric oxide (NO) concentration and gene expression of different inflammatory mediators, i.e., interleukin (IL)-6, tumor necrosis factor (TNF)-a, and IL-1, were measured. sulforaphane neither directly reacted with cytokines, nor with NO. To understand the mechanisms, the authors performed analyses of the expression of regulatory enzyme inducible nitic oxide synthase (iNOS), the transcription factor NF-E2-related factor 2 (Nrf2), and its enzyme heme-oxygenase (HO)-1. The results revealed that LPS increased significantly the expression of inflammatory cytokines and concentration of NO in non-treated cells. sulforaphane was able to prevent the expression of NO and cytokines through regulating inflammatory enzyme iNOS and activation of Nrf2/HO-1 signal transduction pathway [146]. These data are significant because studies have shown both TNF-alpha but also interleukin-6 are involved in pathology of COVID-19 [46, 47, 147-155]. The utilization of sulforaphane as a substitute for anti-IL-6 antibodies would be more economical and potentially without associated toxicity. Other studies have also demonstrated ability of sulforaphane to suppress IL-6 [156-158]. Interestingly, a clinical study was performed in 40 healthy overweight subjects (ClinicalTrials.gov ID NCT 03390855). Treatment phase consisted on the consumption of broccoli sprouts (30 g/day) during 10 weeks and the follow-up phase of 10 weeks of normal diet without consumption of these broccoli sprouts. Anthropometric parameters as body fat mass, body weight, and BMI were determined. Inflammation status was assessed by measuring levels of TNF-a, IL-6, IL-1 and C-reactive protein. IL-6 levels significantly decreased (mean values from 4.76 pg/mL to 2.11 pg/mL with 70 days of broccoli consumption, $p<0.001$) and during control phase the inflammatory levels were maintained at low grade (mean values from 1.20 pg/mL to 2.66 pg/mL, $p<0.001$). C-reactive protein significantly decreased as well [159].

An additional potential benefit of sulforaphane is its ability to protect lungs against damage. It is known that the major cause of lethality associated with COVID-19 is acute respiratory distress syndrome (ARDS). It was demonstrated that sulforaphane is effective in the endotoxin model of this condition. In one experiment, BALB/c mice were treated with sulforaphane (50 mg/kg) and 3 days later, ARDS was induced by the administration of LPS (5 mg/kg). The results revealed that sulforaphane significantly decreased lactate dehydrogenase (LDH) activity (as shown by LDH assay), the wet-to-dry ratio of the lungs and the serum levels of interleukin-6 (IL-6) and tumor necrosis factor-a (TNF-a) (measured by ELISA), as well as nuclear factor-KB protein expression in mice with LPS-induced ARDS. Moreover, treatment with sulforaphane significantly inhibited prostaglandin E2 (PGE2) production, and cyclooxygenase-2 (COX-2), matrix metalloproteinase-9 (MMP-9) protein expression (as shown by western blot analysis), as well as inducible nitric oxide synthase (iNOS) activity in mice with LPS-induced ALI. Lastly, the researchers reported pretreatment with sulforaphane activated the nuclear factor-E2-related factor 2 (Nrf2)/antioxidant response element (ARE) pathway in the mice with LPS-induced ARDS [160].

Epigallocatechin-3-Gallate (EGCG)

EGCG is similar to sulforaphane in that it has been reported to possess cancer preventative properties. This compound has been shown to be one of the top therapeutic ingredients in green tea. It is known from epidemiologic studies that green tea consumption associates with chemoprotective effects against cancer [161-171]. In addition, similarly to sulforaphane, EGCG has been shown to inhibit inflammatory mediators. The first suggestion of this were studies shown suppression of the pro-inflammatory transcription factor NF-kappa B. In a detailed molecular study, EGCG, a potent antitumor agent with anti-inflammatory and antioxidant properties was shown to inhibit nitric oxide (NO) generation as a marker of activated macrophages Inhibition of NO production was observed when cells were cotreated with EGCG and LPS. iNOS activity in soluble extracts of lipopolysaccharide-activated macrophages treated with EGCG (5 and 10 microM) for 6-24 hr was significantly lower than that in macrophages without EGCG treatment. Western blot, reverse transcription-polymerase chain reaction, and Northern blot analyses demonstrated that significantly reduced 130-kDa protein and 4.5-kb mRNA levels of iNOS were expressed in lipopolysaccharide-activated macrophages with EGCG compared with those without EGCG. Electrophoretic mobility shift assay indicated that EGCG blocked the activation of nuclear factor-kappaB, a transcription factor necessary for iNOS induction. EGCG also blocked disappearance of inhibitor kappaB from cytosolic fraction. These results suggest that EGCG decreases the activity and protein levels of iNOS by reducing the expression of iNOS mRNA and the reduction could occur through prevention of the binding of nuclear factor-kappaB to the iNOS promoter [172]. Another study supporting ability of EGCG to suppress NF-kappa B examined a model of atherosclerosis in which exposure of macrophage foam cells to TNF-a results in a downregulation of ABCA1 and a decrease in cholesterol efflux to apoA1, which is attenuated by pretreatment with EGCG. Moreover, rather than activating the Liver X receptor (LXR) pathway, inhibition of the TNF-a-induced nuclear factor-KB (NF-KB) activity is detected with EGCG treatment in cells. In order to inhibit the NF-KB activity, EGCG can promote the dissociation of the nuclear factor E2-related factor 2 (Nrf2)-Kelch-like ECH-associated protein 1 (Keap1) complex; when the released Nrf2 translocates to the nucleus and activates the transcription of genes containing an ARE element inhibition of NF-KB occurs and Keap1 is separated from the complex to directly interact with IKK and thus represses NF-KB function [173].

The anti-inflammatory effects of EGCG can be seen in the ability of this compound to potently inhibit IL-6, the COVID-19 associated cytokine, in a variety of inflammatory settings. For example, in a cardiac infarct model, rats were subjected to myocardial ischemia (30 min) and reperfusion (up to 2 h). Rats were treated with EGCG (10 mg/kg intravenously) or with vehicle at the end of the ischemia period followed by a continuous infusion (EGCG 10 mg/kg/h) during the reperfusion period. In vehicle-treated rats, extensive myocardial injury was associated with tissue neutrophil infiltration as evaluated by myeloperoxidase activity, and elevated levels of plasma creatine phosphokinase. Vehicle-treated rats also demonstrated increased plasma levels of interleukin-6. These events were associated with cytosol degradation of inhibitor kappaB-alpha, activation of IkappaB kinase, phosphorylation of c-Jun, and subsequent activation of nuclear factor-kappaB and activator protein-I in the infarcted heart. In vivo treatment with EGCG reduced myocardial damage and myeloperoxidase activity. Plasma IL-6 and creatine phosphokinase levels were decreased after EGCG administration. This beneficial effect of EGCG was associated with reduction of nuclear factor-kB and activator protein-I DNA binding [174]. In an inflammatory model of ulcerative colitis (UC) mice were randomly divided into four groups: Normal control, model (MD), 50 mg/kg/day EGCG treatment and 100 mg/kg/day EGCG treatment. The daily disease activity index (DAI) of the mice was recorded, changes in the organizational structure of the colon were observed and the spleen index (SI) was measured. In addition, levels of interleukin (IL)-6, IL-10, IL-17 and transforming growth factor (TGF)-1 in the plasma and hypoxia-inducible factor (HIF)-1a and signal transducer and activator of transcription (STAT) 3 protein expression in colon tissues were evaluated. Compared with the MD group, the mice in the two EGCG treatment groups exhibited decreased DA is and S is and an attenuation in the colonic tissue erosion. EGCG could reduce the release of IL-6 and IL-17 and regulate the mouse splenic regulatory T-cell (Treg)/T helper 17 cell (Thl 7) ratio, while increasing the plasma levels of IL-10 and TGF-1 and decreasing the HIF-1a and STAT3 protein expression in the colon. The experiments confirmed that EGCG treated mice with experimental colitis by inhibiting the release of IL-6 and regulating the body Treg/Thl 7 balance [175].

In patients with COVID-19, the ARDS associated with fatality resembles septic shock in many aspects, including DIC, fever, vascular leakage, and systemic inflammation. Wheeler et al. induced polymicrobial sepsis in male Sprague-Dawley rats (hemodynamic study) and C57BL6 mice (mortality study) via cecal ligation and double puncture (CL2P). Rodents were treated with either EGCG (10 mg/kg intraperitoneally) or vehicle at 1 and 6 h after CL2P and every 12 h thereafter. In the hemodynamic study, mean arterial blood pressure was monitored for 18 h, and rats were killed at 3, 6, and 18 h after CL2P. In the mortality study, survival was monitored for 72 h after CL2P in mice. In vehicle-treated rodents, CL2P was associated with profound hypotension and greater than 80% mortality rate. Epigallocatechin-3-gallate treatment significantly improved both the hypotension and survival [176].

A subsequent study by Li et al. showed intraperitoneal administration of EGCG protected mice against lethal endotoxemia, and rescued mice from lethal sepsis even when the first dose was given 24 hours after cecal ligation and puncture. The therapeutic effects were partly attributable to: 1) attenuation of systemic accumulation of proinflammatory mediator (e.g., HMGB1) and surrogate marker (e.g., IL-6 and KC) of lethal sepsis; and 2) suppression of HMGB I-mediated inflammatory responses by preventing clustering of exogenous HMGB1 on macrophage cell surface [177].

Finally, in a lung study, mice were treated with EGCG (10 mg/kg) intraperitoneally (ip) 1 h before LPS injection (10 mg/kg, ip). The results showed that EGCG attenuated LPS-induced ARDS as it decreased the changes in blood gases and reduced the histological lesions, wet-to-dry weight ratios, and myeloperoxidase (MPO) activity. In addition, EGCG significantly decreased the expression of pro-inflammatory cytokines tumor necrosis factor (TNF)-a, interleukin (IL)-1' and IL-6 in the lung, serum, and bronchoalveolar lavage fluid, and alleviated the expression of TLR-4, MyD88, TRIP, and p-p65 in the lung tissue. In addition, it increased the expression of IKB-a and had no influence on the expression of p65. Collectively, these results demonstrated the protective effects of EGCG against LPS-induced ARDS in mice through its anti-inflammatory effect that may be attributed to the suppression of the activation of TLR 4-dependent NF-KB signaling pathways [178].

CONCLUSION

This invention represents an optimized nutraceutical blend formulated for inhibiting viral entry through stimulation of NK cells, suppressing viral proliferation through modulating the viral life cyclic, and dampening pathological inflammatory responses in order to allow the lungs sufficient protection from the ongoing cytokine storm. We anticipate to initiate clinical trials both in healthy volunteers at high risk of infection, and for infected patients.

REFERENCES

1. Zheng, J., *SARS-CoV-2: an Emerging Coronavirus that Causes a Global Threat*. Int J Biol Sci, 2020. 16(10): p. 1678-1685.
2. Zhang, T., Q. Wu, and Z. Zhang, *Probable Pangolin Origin of SARS-CoV-2 Associated with the COVID-19 Outbreak*. Curr Biol, 2020. 30(7): p. 1346-1351 e2.
3. Walls, A. C., et al., *Structure, Function, and Antigenicity of the SARS-CoV-2 Spike Glycoprotein*. Cell, 2020. 181 (2): p. 281-292 e6.
4. Tian, X., et al., *Potent binding of 2019 novel coronavirus spike protein by a SARS coronavirus-specifzc human monoclonal antibody*. Emerg Microbes Infect, 2020. 9(1): p. 382-385.
5. Zheng, M. and L. Song, *Novel antibody epitopes dominate the antigenicity of spike glycoprotein in SARS-CoV-2 compared to SARS-CoV* Cell Mol Immunol, 2020.
6. Stadlbauer, D., et al., *SARS-CoV-2 Seroconversion in Humans: A Detailed Protocol for a Serological Assay, Antigen Production, and Test Setup*. Curr Protoc Microbial, 2020. 57(1): p. e1 00.
7. de Wilde, A. H., et al., *Host Factors in Coronavirus Replication*. Curr Top Microbial Immunol, 2018. 419: p. 1-42.
8. Raj, V. S., et al., *Dipeptidyl peptidase 4 is a functional receptor for the emerging human coronavirus-EMC*. Nature, 2013. 495(7440): p. 251-4.
9. Xia, S., et al., *Inhibition of SARS-CoV-2 (previously 2019-nCoV) infection by a highly potent pan-coronavirus fusion inhibitor targeting its spike protein that harbors a high capacity to mediate membrane fusion*. Cell Res, 2020.
10. Sevajol, M., et al., *Insights into RNA synthesis, capping, and proofreading mechanisms of SARS-coronavirus*. Virus Res, 2014. 194: p. 90-9.
11. Wu, D., et al., *The SARS-CoV-2 outbreak: what we know*. Int J Infect Dis, 2020.
12. Lu, R., et al., *Genomic characterisation and epidemiology of 2019 novel coronavirus: implications for virus origins and receptor binding*. Lancet, 2020. 395(10224): p. 565-574.
13. Zhu, N., et al., *A Novel Coronavirus from Patients with Pneumonia in China, 2019*. N Engl J Med, 2020. 382(8): p. 727-733.
14. Stower, H., *Virological assessment of SARS-CoV-2*. Nat Med, 2020. 26(4): p. 465.
15. Lovato, A. and C. de Filippis, *Clinical Presentation of COVID-19: A Systematic Review Focusing on Upper Airway Symptoms*. Ear Nose Throat J, 2020: p. 145561320920762.
16. Chan, J. F., et al., *A familial cluster of pneumonia associated with the 2019 novel coronavirus indicating* person-to-person transmission: a study of a family cluster. Lancet, 2020. 395(10223): p. 514-523.
17. Chen, N., et al., *Epidemiological and clinical characteristics of 99 cases of 2019 novel coronavirus pneumonia in Wuhan, China: a descriptive study.* Lancet, 2020. 395(10223): p. 507-513.
18. Holshue, M. L., et al., *First Case of 2019 Novel Coronavirus in the United States.* N Engl J Med, 2020. 382(10): p. 929-936.
19. Wu, S. C., *Progress and Concept for COVID-19 Vaccine Development.* Biotechnol J, 2020: p. e2000147.
20. Chen, W. H., et al., *The SARS-CoV-2 Vaccine Pipeline: an Overview.* Curr Trop Med Rep, 2020: p. 1-4.
21. Amanat, F. and F. Krammer, *SARS-CoV-2 Vaccines: Status Report.* Immunity, 2020. 52(4): p. 583-589.
22. Hyun-Jung Lee, C. and H. Koohy, *In silica identification of vaccine targets for 2019-nCoV* FlOOORes, 2020. 9: p. 145.
23. Ayoub, B. M., *COVID-19 vaccination clinical trials should consider multiple doses of BCG.* Pharmazie, 2020. 75(4): p. 159.
24. Gursel, M. and I. Gursel, *Is global ECG vaccination-induced trained immunity relevant to the progression of SARS-CoV-2 pandemic?* Allergy, 2020.
25. Redelman-Sidi, G., *Could ECG be used to protect against COVID-19?* Nat Rev Urol, 2020.
26. Stahlmann, R. and H. Lode, *Medication for COVID-19-an Overview of Approaches Currently Under Study.* Dtsch Arztebl Int, 2020. 117(13): p. 213-219.
27. Wang, M., et al., *Remdesivir and chloroquine effectively inhibit the recently emerged novel coronavirus (2019-nCoV) in vitro.* Cell Res, 2020. 30(3): p. 269-271.
28. Elfiky, A. A., *Anti-HCV, nucleotide inhibitors, repurposing against COVID-19.* Life Sci, 2020. 248: p. 117477.
29. Al-Tawfiq, J. A., A. H. Al-Homoud, and Z. A. Memish, *Remdesivir as a possible therapeutic option for the COVID-19.* Travel Med Infect Dis, 2020: p. 101615.
30. Chen, L., et al., *Convalescent plasma as a potential therapy for COVID-19.* Lancet Infect Dis, 2020. 20(4): p. 398-400.
31. Tanne, J. H., *Covid-19: FDA approves use of convalescent plasma to treat critically ill patients.* BMJ, 2020. 368: p. m1256.
32. Shen, C., et al., *Treatment of 5 Critically Ill Patients With COVID-19 With Convalescent Plasma.* JAMA, 2020.
33. Duan, K., et al., *Effectiveness of convalescent plasma therapy in severe COVID-19 patients.* Proc Natl Acad Sci USA, 2020. 117(17): p. 9490-9496.
34. Bloch, E. M., et al., *Deployment of convalescent plasma for the prevention and treatment of COVID-19.* J Clin Invest, 2020.
35. Ahn, J. Y., et al., *Use of Convalescent Plasma Therapy in Two COVID-19 Patients with Acute Respiratory Distress Syndrome in Korea.* J Korean Med Sci, 2020. 35(14): p. e1 49.
36. Ye, M., et al., *Treatment with convalescent plasma for COVID-19 patients in Wuhan, China.* J Med Viral, 2020.
37. Zhao, Q. and Y. He, *Challenges a/Convalescent Plasma Therapy on COVID-19.* J Clin Viral, 2020. 127: p. 104358.
38. Langhi, D. M., G. C. Santis, and J. O. Bordin, *COVID-19 convalescent plasma transfusion.* Hematol Transfus Cell Tuer, 2020.
39. Brown, B. L. and J. McCullough, *Treatment for emerging viruses: Convalescent plasma and COVID-19.* Transfus Apher Sci, 2020: p. 102790.
40. Zeng, Q. L., et al., *Effect of Convalescent Plasma Therapy on Viral Shedding and Survival in COVID-19 Patients.* J Infect Dis, 2020.
41. Zhang, W., et al., *The use of anti-inflammatory drugs in the treatment of people with severe coronavirus disease 2019 (COVID-19): The Perspectives of clinical immunologists. from China.* Clin Immunol, 2020. 214: p. 108393.
42. Russell, B., et al., *Associations between immune-suppressive and stimulating drugs and novel COVID-19-a systematic review of current evidence.* Ecancermedicalscience, 2020. 14: p. 1022.
43. Napolitano, M., G. Fabbrocini, and C. Patruno, *Potential role of Janus kinase inhibitors in COVID-19.* J Am Acad Dermatol, 2020.
44. Peterson, D., W. Damsky, and B. King, *Calm before the storm: understanding the role of JAK inhibitors in COVID-19.* J Am Acad Dermatol, 2020.
45. Bennardo, F., C. Buffone, and A. Giudice, *New therapeutic opportunities for COVID-19 patients with Tocilizumab: Possible correlation of interleukin-6 receptor inhibitors with osteonecrosis of the jaws.* Oral Oncol, 2020: p. 104659.
46. Zhang, C., et al., *The cytokine release syndrome (CRS) of severe COVID-19 and Interleukin-6 receptor (IL-6R) antagonist Tocilizumab may be the key to reduce the mortality.* Int J Antimicrob Agents, 2020: p. 105954.
47. Zhang, X., et al., *First case of COVID-19 in a patient with multiple myeloma successfully treated with tocilizumab.* Blood Adv, 2020. 4(7): p. 1307-1310.
48. Michot, J. M., et al., *Tocilizumab, an anti-IL6 receptor antibody, to treat Covid-19-related respiratory failure: a case report.* Ann Oncol, 2020.
49. Cellina, M., et al., *Favorable changes of CT findings in a patient with COVID-19 pneumonia after treatment with tocilizumab.* Diagn Intery Imaging, 2020.
50. Ortiz-Martinez, Y., *Tocilizumab: A new opportunity in the possible therapeutic arsenal against COVID-19.* Travel Med Infect Dis, 2020: p. 101678.
51. Cron, R. Q. and W. W. Chatham, *The Rheumatologist's Role in COVID-19.* J Rheumatol, 2020.
52. Monteagudo, L. A., A. Boothby, and E. Gertner, *Continuous Intravenous Anakinra Infusion to Calm the Cytokine Storm in Macrophage Activation Syndrome.* ACR Open Rheumatol, 2020.
53. Cron, R. Q. and W. W. Chatham, *The Question of Whether to Remain on Therapy for Chronic Rheumatic Diseases in the Setting of the Covid-19 Pandemic.* J Rheumatol, 2020.
54. Leng, Z., et al., *Transplantation of ACE2(−) Mesenchymal Stem Cells Improves the Outcome of Patients with COVID-19 Pneumonia.* Aging Dis, 2020. 11(2): p. 216-228.
55. Atluri, S., L. Manchikanti, and J. A. Hirsch, *Expanded Umbilical CordMesenchymal Stem Cells (UC-MSCs) as a Therapeutic Strategy in Managing Critically Ill COVID-19 Patients: The Case for Compassionate Use.* Pain Physician, 2020. 23(2): p. E71-E83.
56. Shetty, A. K., *Mesenchymal Stem Cell Infasion Shows Promise for Combating Coronavirus (COVID-19)-InducedPneumonia.* Aging Dis, 2020.11(2): p. 462-464.
57. Khoury, M., et al., *Current Status of Cell-Based Therapies for Respiratory Virus Infections: Applicability to COVID-19.* Eur Respir J, 2020.
58. Golchin, A., E. Seyedjafari, and A. Ardeshirylajimi, *Mesenchymal Stem Cell Therapy for COVID-19: Present or Future.* Stem Cell Rev Rep, 2020.

59. Bari, E., et al., *Mesenchymal Stramal Cell Secretome for Severe COVID-19 Infections: Premises for the Therapeutic Use*. Cells, 2020. 9(4).
60. Zhao, R. C., *Stem Cell-Based Therapy for Coronavirus Disease 2019*. Stem Cells Dev, 2020.
61. Chen, J., et al., *Clinical study of mesenchymal stem cell treating acute respiratory distress syndrome induced by epidemic Influenza A (H7N9) infection, a hint for COVID-19 treatment*. Engineering (Beijing), 2020.
62. Metcalfe, S. M., *Mesenchymal stem cells and management of COVID-19 pneumonia*. Med Drug Discov, 2020. 5: p. 100019.
63. Ji, F., et al., *Mesenchymal stem cells as a potential treatment for critically ill patients with coronavirus disease 2019*. Stem Cells Transl Med, 2020.
64. Gentile, P. and A. Sterodimas, *Adipose-derived stromal stem cells (ASCs) as a new regenerative immediate therapy combating coronavirus (COVID-19)-induced pneumonia*. Expert Opin Biol Tuer, 2020: p. 1-6.
65. Schindler, L., H. Engler, and H. Kirchner, *Activation of natural killer cells and induction of interferon after injection of mouse hepatitis virus type 3 in mice*. Infect Immun, 1982. 35(3): p. 869-73.
66. Carman, P. S., et al., *Natural killer (NK) cell activity against enteric murine coronavirus mediated by intestinal leukocytes*. Adv Exp Med Biol, 1987. 216A: p. 533-7.
67. Lehoux, M., et al., *Murine viral hepatitis involves NK cell depletion associated with virus-induced apoptosis*. Clin Exp Immunol, 2004. 137(1): p. 41-51.
68. Bao, M., et al., *Anti-SARS-CoV immunity induced by a novel CpG oligodeoxynucleotide*. Clin Immunol, 2006. 118(2-3): p. 180-7.
69. Wang, D., et al., *Clinical Characteristics of 138 Hospitalized Patients With 2019 Novel Coronavirus-Infected Pneumonia in Wuhan, China*. JAMA, 2020.
70. Channappanavar, R. and S. Perlman, *Pathogenic human coronavirus infections: causes and consequences of cytokine storm and immunopathology*. Semin Immunopathol, 2017. 39(5): p. 529-539.
71. Bellani, G., et al., *Epidemiology, Patterns of Care, and Mortality for Patients With Acute Respiratory Distress Syndrome in Intensive Care Units in 50 Countries*. JAMA, 2016. 315(8): p. 788-800.
72. Roten, R., et al., *Plasma levels of tumor necrosis factor in the adult respiratory distress syndrome*. Am Rev Respir Dis, 1991. 143(3): p. 590-2.
73. Sheng, W. H., et al., *Clinical manifestations and inflammatory cytokine responses in patients with severe acute respiratory syndrome*. J Formos Med Assoc, 2005. 104 (10): p. 715-23.
74. Romaschin, A. D., et al., *Systemic phospholipase A2 and cachectin levels in adult respiratory distress syndrome and multiple-organ failure*. Clin Biochem, 1992. 25(1): p. 55-60.
75. Koh, Y., et al., *Tumor necrosis factor induced acute lung leak in rats: less than with interleukin-J*. Inflammation, 1996. 20(5): p. 461-9.
76. Dunican, A. L., et al., *TNFalpha-induced suppression of PMN apoptosis is mediated through interleukin-8 production*. Shock, 2000. 14(3): p. 284-8; discussion 288-9.
77. Negrier, M. S., et al., *Phase I trial of recombinant interleukin-2/ollowed by recombinant tumor necrosis factor in patients with metastatic cancer*. J Immunother (1991), 1992. 11(2): p. 93-102.
78. Malemud, C. J., *Recent advances in neutralizing the IL-6 pathway in arthritis*. Open Access Rheumatol, 2009. 1: p. 133-150.
79. Romagnani, S., *Human Thi 7 cells*. Arthritis Res Tuer, 2008. 10(2): p. 206.
80. Romagnani, S., et al., *Properties and origin of human Thi 7 cells*. Mol Immunol, 2009. 47(1): p. 3-7.
81. Kimura, A. and T. Kishimoto, *IL-6: regulator o/Treg/Thl7 balance*. Eur J Immunol, 2010. 40(7): p. 1830-5.
82. Yu, Z. X., et al., *The ratio of Thi 7/Treg cells as a risk indicator in early acute respiratory distress syndrome*. Crit Care, 2015. 19: p. 82.
83. Mock, J. R., et al., *Foxp3+ regulatory T cells promote lung epithelial proliferation*. Mucosal Immunol, 2014. 7(6): p. 1440-51.
84. Kimura, A. and T. Kishimoto, *Thl7 cells in inflammation*. Int Immunopharmacol, 2011. 11(3): p. 319-22.
85. Meduri, G. U., et al., *Persistent elevation of inflammatory cytokines predicts a poor outcome in ARDS. Plasma IL-1 beta and IL-6 levels are consistent and efficient predictors of outcome over time*. Chest, 1995. 107(4): p. 1062-73.
86. Hui, L., et al., *Higher serum procalcitonin and IL-6 levels predict worse diagnosis for acute respiratory distress syndrome patients with multiple organ dysfanction*. Int J Clin Exp Pathol, 2017. 10(7): p. 7401-7407.
87. Swaroopa, D., et al., *Association of serum interleukin-6, interleukin-8, and Acute Physiology and Chronic Health Evaluation II score with clinical outcome in patients with acute respiratory distress syndrome*. Indian J Crit Care Med, 2016. 20(9): p. 518-25.
88. Bime, C., et al., *Development of a biomarker mortality risk model in acute respiratory distress syndrome*. Crit Care, 2019. 23(1): p. 410.
89. Spadaro, S., et al., *Biomarkers for Acute Respiratory Distress syndrome and prospects for personalised medicine*. J Inflamm (Lond), 2019. 16: p. 1.
90. McCormack, D. and D. McFadden, *A review of pterostilbene antioxidant activity and disease modification*. Oxid Med Cell Longev, 2013. 2013: p. 575482.
91. Paul, B., et al., *Occurrence of resveratrol and pterostilbene in age-old darakchasava, an ayurvedic medicine from India*. J Ethnopharmacol, 1999. 68(1-3): p. 71-6.
92. Kapetanovic, I. M., et al., *Pharmacokinetics, oral bioavailability, and metabolic profile of resveratrol and its dimethylether analog, pterostilbene, in rats*. Cancer Chemother Pharmacol, 2011. 68(3): p. 593-601.
93. Perecko, T., et al., *Molecular targets of the natural antioxidant pterostilbene: effect on protein kinase C, caspase-3 and apoptosis in human neutrophils in vitro*. Neuro Endocrinol Lett, 2010. 31 Suppl 2: p. 84-90.
94. Stivala, L. A., et al., *Specific structural determinants are responsible for the antioxidant activity and the cell cycle effects of resveratrol*. J Biol Chem, 2001. 276(25): p. 22586-94.
95. Athar, M., et al., *Resveratrol: a review of preclinical studies for human cancer prevention*. Toxicol Appl Pharmacol, 2007. 224(3): p. 274-83.
96. Bishayee, A., *Cancer prevention and treatment with resveratrol: from rodent studies to clinical trials*. Cancer Prev Res (Phila), 2009. 2(5): p. 409-18.
97. Hsu, C. L., et al., *The inhibitory effect of pterostilbene on inflammatory responses during the interaction of 3T3-Ll adipocytes and RAW 264.7 macrophages*. J Agric Food Chem, 2013. 61(3): p. 602-10.
98. McCormack, D., D. McDonald, and D. McFadden, *Pterostilbene ameliorates tumor necrosis factor alpha-induced pancreatitis in vitro*. J Surg Res, 2012. 178(1): p. 28-32.

99. Erasalo, H., et al., *Natural Stilbenoids Have Anti-Inflammatory Properties in Vivo and Down-Regulate the Production of Inflammatory Mediators NO, IL6, and MCP1 Possibly in a P13KIAkt-Dependent Manner.* J Nat Prod, 2018. 81(5): p. 1131-1142.
100. Allijn, I. E., et al., *Head-to-Head Comparison of Anti-Inflammatory Performance of Known Natural Products In Vitro.* PLoS One, 2016. 11(5): p. e0155325.
101. Meng, X. L., et al., *Effects of resveratrol and its derivatives on lipopolysaccharide-induced microglial activation and their structure-activity relationships.* Chem Biol Interact, 2008. 174(1): p. 51-9.
102. Zhang, L., et al., *Pterostilbene protects vascular endothelial cells against oxidized low-density lipoprotein-induced apoptosis in vitro and in vivo.* Apoptosis, 2012. 17(1): p. 25-36.
103. Park, S. H., et al., *Pterostilbene, an Active Constituent of Blueberries, Stimulates Nitric Oxide Production via Activation of Endothelial Nitric Oxide Synthase in Human Umbilical Vein Endothelial Cells.* Plant Foods Hum Nutr, 2015. 70(3): p. 263-8.
104. Chen, Z. W., et al., *Pterostilbene protects against uraemia serum-induced endothelial cell damage via activation of Keapl/Nrj2/HO-l signaling.* Int Urol Nephrol, 2018. 50(3): p. 559-570.
105. Chen, C., et al., *Effect of resveratrol combined with atorvastatin on re-endothelialization after drug-eluting stents implantation and the underlying mechanism.* Life Sci, 2020. 245: p. 117349.
106. Bekpinar, S., et al., *Resveratrol ameliorates the cyclosporine-induced vascular and renal impairments: possible impact of the modulation of renin-angiotensin system.* Can J Physiol Pharmacol, 2019. 97(12): p. 1115-1123.
107. Swamy, S. M. and B. K. Tan, *Cytotoxic and immunopotentiating effects of ethanolic extract of Nigella sativa L. seeds.* J Ethnopharmacol, 2000. 70(1): p. 1-7.
108. Salem, M. L., F. Q. Alenzi, and W. Y. Attia, *Thymoquinone, the active ingredient of Nigella sativa seeds, enhances survival and activity of antigen-specific CDS-positive T cells in vitro.* Br J Biomed Sci, 2011. 68(3): p. 131-7.
109. Majdalawieh, A. F., R. Hmaidan, and R. I. Carr, *Nigella sativa modulates splenocyte proliferation, Thl/Th2 cytokine profile, macrophage function and NK anti-tumor activity.* J Ethnopharmacol, 2010. 131(2): p. 268-75.
110. Salomi, M. J., et al., *Anti-cancer activity of nigella sativa.* Anc Sci Life, 1989. 8(3-4): p. 262-6.
111. Salomi, N. J., et al., *Antitumour principles from Nigella sativa seeds.* Cancer Lett, 1992. 63(1): p. 41-6.
112. Ait Mbarek, L., et al., *Anti-tumor properties of blackseed (Nigella sativa L.) extracts.* Braz J Med Biol Res, 2007. 40(6): p. 839-47.
113. Amara, A. A., M. H. El-Masry, and H. H. Bogdady, *Plant crude extracts could be the solution: extracts showing in vivo antitumorigenic activity.* Pak J Phann Sci, 2008. 21(2): p. 159-71.
114. Banerjee, S., et al., *Review on molecular and therapeutic potential of thymoquinone in cancer.* Nutr Cancer, 2010. 62(7): p. 938-46.
115. Khan, M. A., et al., *Anticancer activities of Nigella sativa (black cumin).* Afr J Tradit Complement Ahem Med, 2011. 8(5 Suppl): p. 226-32.
116. Woo, C. C., et al., *Thymoquinone: potential cure for inflammatory disorders and cancer.* Biochem Pharmacol, 2012. 83(4): p. 443-51.
117. Lei, X., et al., *Thymoquinone inhibits growth and augments 5-jluorouracil-induced apoptosis in gastric cancer cells both in vitro and in vivo.* Biochem Biophys Res Commun, 2012. 417(2): p. 864-8.
118. Linjawi, S. A., et al., *Evaluation of the protective effect of Nigella sativa extract and its primary active component thymoquinone against DMBA-induced breast cancer in female rats.* Arch Med Sci, 2015. 11(1): p. 220-9.
119. Majdalawieh, A. F. and M. W. Fayyad, *Recent advances on the anti-cancer properties of Nigella sativa, a widely used food additive.* J Ayurveda Integr Med, 2016. 7(3): p. 173-180.
120. Majdalawieh, A. F., M. W. Fayyad, and G. K. Nasrallah, *Anti-cancer properties and mechanisms of action of thymoquinone, the major active ingredient of Nigella sativa.* Crit Rev Food Sci Nutr, 2017. 57(18): p. 3911-3928.
121. Mostofa, A. G. M., et al., *Thymoquinone as a Potential Adjuvant Therapy for Cancer Treatment: Evidence from Preclinical Studies.* Front Pharmacol, 2017. 8: p. 295.
122. Asaduzzaman Khan, M., et al., *Thymoquinone, as an anticancer molecule: from basic research to clinical investigation.* Oncotarget, 2017. 8(31): p. 51907-51919.
123. Imran, M., et al., *Thymoquinone: A novel strategy to combat cancer: A review.* Biomed Pharmacother, 2018. 106: p. 390-402.
124. Zhang, Y., et al., *Thymoquinone inhibits the metastasis of renal cell cancer cells by inducing autophagy via AMPK/mTOR signaling pathway.* Cancer Sci, 2018. 109 (12): p. 3865-3873.
125. Ulasli, M., et al., *The effects of Nigella sativa (Ns), Anthemis hyalina (Ah) and Citrus sinensis (Cs) extracts on the replication of coronavirus and the expression of TRP genes family.* Mol Biol Rep, 2014. 41(3): p. 1703-11.
126. Ahmad, A., et al., *A review on therapeutic potential of Nigella sativa: A miracle herb.* Asian Pac J Trop Biomed, 2013. 3(5): p. 337-52.
127. Alemi, M., et al., *Anti-inflammatory effect of seeds and callus of Nigella sativa L. extracts on mix glial cells with regard to their thymoquinone content.* AAPS PharmSciTech, 2013. 14(1): p. 160-7.
128. Shuid, A. N., et al., *Nigella sativa: A Potential Antiosteoporotic Agent.* Evid Based Complement Altemat Med, 2012. 2012: p. 696230.
129. El Mezayen, R., et al., *Effect of thymoquinone on cyclooxygenase expression and prostaglandin production in a mouse model of allergic airway inflammation.* Immunol Lett, 2006. 106(1): p. 72-81.
130. Chehl, N., et al., *Anti-inflammatory effects of the Nigella sativa seed extract, thymoquinone, in pancreatic cancer cells.* HPB (Oxford), 2009. 11(5): p. 373-81.
131. Alkharfy, K. M., et al., *The protective effect of thymoquinone against sepsis syndrome morbidity and mortality in mice.* Int Immunopharmacol, 2011. 11(2): p. 250-4.
132. Shen, G., et al., *Chemoprevention of familial adenomatous polyposis by natural dietary compounds sulforaphane and dibenzoylmethane alone and in combination in ApcMinl+ mouse.* Cancer Res, 2007. 67(20): p. 9937-44.
133. Zambrano, V., R. Bustos, and A. Mahn, *Insights about stabilization of sulforaphane through microencapsulation.* Heliyon, 2019. 5(11): p. e0295 1.
134. Steinkellner, H., et al., *Effects of cruciferous vegetables and their constituents on drug metabolizing enzymes involved in the bioactivation of DNA-reactive dietary carcinogens.* Mutat Res, 2001. 480-481: p. 285-97.
135. Fahey, J. W., Y. Zhang, and P. Talalay, *Broccoli sprouts: an exceptionally rich source of inducers of enzymes that*

136. Solowiej, E., et al., *Chemoprevention of cancerogenesis—the role of sulforaphane*. Acta Pol Phann, 2003. 60(1): p. 97-100.
137. Gills, J. J., et al., *Sulforaphane prevents mouse skin tumorigenesis during the stage of promotion*. Cancer Lett, 2006. 236(1): p. 72-9.
138. Myzak, M. C., et al., *Sulforaphane inhibits histone deacetylase in vivo and suppresses tumorigenesis in Apeminus mice*. FASEB J, 2006. 20(3): p. 506-8.
139. Singh, A. V., et al., *Sulforaphane induces caspase-mediated apoptosis in cultured PC-3 human prostate cancer cells and retards growth of PC-3 xenografts in vivo*. Carcinogenesis, 2004. 25(1): p. 83-90.
140. Wang, L., et al., *Targeting cell cycle machinery as a molecular mechanism of sulforaphane in prostate cancer prevention*. Int J Oncol, 2004. 24(1): p. 187-92.
141. Pham, N. A., et al., *The dietary isothiocyanate sulforaphane targets pathways of apoptosis, cell cycle arrest, and oxidative stress in human pancreatic cancer cells and inhibits tumor growthin severe combined immunodeficient mice*. Mol Cancer Tuer, 2004. 3(10): p. 1239-48.
142. Thejass, P. and G. Kuttan, *Antimetastatic activity of Sulforaphane*. Life Sci, 2006. 78(26): p. 3043-50.
143. Fimognari, C. and P. Hreha, *Sulforaphane as a promising molecule for fighting cancer*. Mutat Res, 2007. 635(2-3): p. 90-104.
144. Li, Y., et al., *Sulforaphane, a dietary component of broccoli/broccoli sprouts, inhibits breast cancer stem cells*. Clin Cancer Res, 2010. 16(9): p. 2580-90.
145. Lin, W., et al., *Sulforaphane suppressed LPS-induced inflammation in mouse peritoneal macrophages through Nrj2 dependent pathway*. Biochem Pharmacol, 2008. 76(8): p. 967-73.
146. Ruhee, R. T., S. Ma, and K. Suzuki, *Sulforaphane Protects Cells against Lipopolysaccharide—Stimulated Inflammation in Murine Macrophages*. Antioxidants (Basel), 2019. 8(12).
147. Xu, X., et al., *Effective treatment of severe COVID-19 patients with tocilizumab*. Proc Natl Acad Sci USA, 2020.
148. Liu, F., et al., *Prognostic value of interleukin-6, C-reactive protein, and procalcitonin in patients with COVID-19*. J Clin Viral, 2020. 127: p. 104370.
149. Aziz, M., R. Fatima, and R. Assaly, *Elevated Interleukin-6 and Severe COVID-19: A Meta-Analysis*. J Med Viral, 2020.
150. Chen, X., et al., *Detectable serum SARS-CoV-2 viral load (RNAaemia) is closely correlated with drastically elevated interleukin 6 (IL-6) level in critically ill COVID-19 patients*. Clin Infect Dis, 2020.
151. McGonagle, D., et al., *The Role o/Cytokines including Interleukin-6 in COVID-19 induced Pneumonia and Macrophage Activation Syndrome-Like Disease*. Autoimmun Rev, 2020: p. 102537.
152. Luo, P., et al., *Tocilizumab treatment in COVID-19: A single center experience*. J Med Viral, 2020.
153. Ulhaq, Z. S. and G. V. Soraya, *Interleukin-6 as a potential biomarker of COVID-19 progression*. Med Mal Infect, 2020.
154. Fu, B., X. Xu, and H. Wei, *Why tocilizumab could be an effective treatment for severe COVID-19?* J Transl Med, 2020. 18(1): p. 164.
155. Liu, B., et al., *Can we use interleukin-6 (IL-6) blockade for coronavirus disease 2019 (COVID-19)-induced cytokine release syndrome (CRS)?* J Autoimmun, 2020: p. 102452.
156. Eren, E., et al., *Sulforaphane Inhibits Lipopolysaccharide-Induced Inflammation, Cytotoxicity, Oxidative Stress, and miR-155 Expression and Switches to Mox Phenotype through Activating Extracellular Signal-Regulated Kinase 112-Nuclear Factor Erythroid 2-Related Factor 2/Antioxidant Response Element Pathway in Murine Microglial Cells*. Front Immunol, 2018. 9: p. 36.
157. Ma, T., et al., *Sulforaphane, a Natural Isothiocyanate Compound, Improves Cardiac Function and Remodeling by Inhibiting Oxidative Stress and Inflammation in a Rabbit Model of Chronic Heart Failure*. Med Sci Monit, 2018. 24: p. 1473-1483.
158. Liu, H., et al., *Biomarker Exploration in Human Peripheral Blood Mononuclear Cells for Monitoring Sulforaphane Treatment Responses in Autism Spectrum Disorder*. Sci Rep, 2020. 10(1): p. 5822.
159. Lopez-Chillon, M. T., et al., *Effects of long-term consumption of broccoli sprouts on inflammatory markers in overweight subjects*. Clin Nutr, 2019. 38(2): p. 745-752.
160. Qi, T., et al., *Sulforaphane exerts anti-inflammatory effects against lipopolysaccharide-induced acute lung injury in mice through the Nrj2/ARE pathway*. Int J Mol Med, 2016. 37(1): p. 182-8.
161. Dashwood, R. H., et al., *Cancer chemopreventive mechanisms of tea against heterocyclic amine mutagens from cooked meat*. Proc Soc Exp Biol Med, 1999. 220(4): p. 239-43.
162. Brown, M. D., *Green tea (Camellia sinensis) extract and its possible role in the prevention of cancer*. Ahem Med Rev, 1999. 4(5): p. 360-70.
163. Banerjee, S., et al., *Black tea polyphenols restrict benzopyrene-induced mouse lung cancer progression through inhibition of Cox-2 and induction of caspase-3 expression*. Asian Pac J CancerPrev, 2006. 7(4): p. 661-6.
164. Shimizu, M., Y. Shirakami, and H. Moriwaki, *Targeting receptor tyrosine kinases for chemoprevention by green tea catechin, EGCG*. Int J Mol Sci, 2008. 9(6): p. 1034-49.
165. Johnson, J. J., H. H. Bailey, and H. Mukhtar, *Green tea polyphenols for prostate cancer chemoprevention: a translational perspective*. Phytomedicine, 2010. 17(1): p. 3-13.
166. Kim, J. W., A. R. Amin, and D. M. Shin, *Chemoprevention of head and neck cancer with green tea polyphenols*. Cancer Prev Res (Phila), 2010. 3(8): p. 900-9.
167. Henning, S. M., P. Wang, and D. Heber, *Chemopreventive effects of tea in prostate cancer: green tea versus black tea*. Mol Nutr Food Res, 2011. 55(6): p. 905-20.
168. Du, G. J., et al., *Epigallocatechin Gallate (EGCG) is the most effective cancer chemopreventive polyphenol in green tea*. Nutrients, 2012. 4(11): p. 1679-91.
169. Henning, S. M., et al., *Phenolic acid concentrations in plasma and urine from men consuming green or black tea and potential chemopreventive properties for colon cancer*. Mol Nutr Food Res, 2013. 57(3): p. 483-93.
170. Schramm, L., *Going Green: The Role of the Green Tea Component EGCG in Chemoprevention*. J Carcinog Mutagen, 2013. 4(142): p. 1000142.
171. Rahmani, A. H., et al., *Implications of Green Tea and Its Constituents in the Prevention of Cancer via the Modulation of Cell Signalling Pathway*. Biomed Res Int, 2015. 2015: p. 925640.
172. Lin, Y. L. and J. K. Lin, *(-)-Epigallocatechin-3-gallate blocks the induction of nitric oxide synthase by down-* regulating lipopolysaccharide-induced activity of transcription factor nuclear factor-kappaB. Mol Pharmacol, 1997. 52(3): p. 465-72.
173. Jiang, J., et al., *Epigallocatechin-3-gallate prevents TNF-alpha-induced NF-kappaB activation thereby upregulating ABCAJ via the Nrj2/Keapl pathway in macrophage foam cells*. Int J Mol Med, 2012. 29(5): p. 946-56.
174. Aneja, R., et al., *Epigallocatechin, a green tea polyphenol, attenuates myocardial ischemia reperfusion injury in rats*. Mol Med, 2004. 10(1-6): p. 55-62.
175. Xu, Z., et al., *Epigallocatechin-3-gallate-induced inhibition of interleukin-6 release and adjustment of the regulatory TIT helper 17 cell balance in the treatment of colitis in mice*. Exp Tuer Med, 2015. 10(6): p. 2231-2238.
176. Wheeler, D. S., et al., *The green tea polyphenol epigallocatechin-3-gallate improves systemic hemodynamics and survival in rodent models of polymicrobial sepsis*. Shock, 2007. 28(3): p. 353-9.
177. Li, W., et al., *A major ingredient of green tea rescues mice from lethal sepsis partly by inhibiting HMGBJ*. PLoS One, 2007. 2(11): p. e1153.
178. Wang, J., S. M. Fan, and J. Zhang, *Epigallocatechin-3-gallate ameliorates lipopolysaccharide-induced acute lung injury by suppression of TLR4/NF-kappaB signaling activation*. Braz J Med Biol Res, 2019. 52(7): p. e8092.

The invention claimed is:

1. A method of treating or preventing complications associated with a SARS-CoV-2 infection, comprising: administration of a combination comprising a) Green Tea and/or extract thereof; b) Blueberry and/or extract thereof; c) *Nigella Sativa* and/or extract thereof; and d) broccoli and/or extract thereof in an amount and frequency sufficient to treat or prevent complications associated with said SARS-CoV-2 infection.

2. The method of claim 1, wherein said green tea extract is epigallocatechin-3-gallate or an analogue thereof, said blueberry extract is pterostilbene or an analogue thereof, said *Nigella Sativa* extract is thymoquinone or an analogue thereof, and said broccoli extract is sulforaphane or an analogue thereof.

3. The method of claim 1, wherein said combination is administered at a dosage and frequency sufficient to inhibit viral establishment into the host.

4. The method of claim 3, wherein inhibition of viral establishment into the host is accomplished by enhancement of natural killer cell activity.

5. The method of claim 3, wherein inhibition of viral establishment into the host is accomplished by enhancement of interferon production.

6. The method of claim 1, wherein said combination is administered at a dosage and frequency sufficient to inhibit viral replication into the host.

7. The method of claim 6, wherein said viral replication in the host is associated with suppression of the viral life cycle.

8. The method of claim 1, wherein said combination decreases propensity towards acute respiratory distress syndrome (ARDS).

9. The method of claim 8, wherein said ARDS is associated with enhanced monocytic accumulation in the alveolar space.

10. The method of claim 9, wherein said monocytes of said monocytic accumulation are of the M1 lineage.

11. The method of claim 9, wherein said monocytes of said monocytic accumulation are of the M2 lineage.

12. The method of claim 8, wherein said ARDS is associated with enhanced neutrophil accumulation in the alveolar space.

13. The method of claim 12, wherein said neutrophils are activated.

14. The method of claim 13, wherein said activated neutrophils produce matrix metalloproteases.

15. The method of claim 1, wherein said composition reduces expression of inflammatory markers.

16. The method of claim 15, wherein said inflammatory markers are selected from the group consisting of: Cluster of differentiation 40 ligand (CD-40L), Eotaxin, fibrinogen, growth hormone (GH), keratinocyte-derived cytokine (KC/GRO), interleukin-I.beta. (IL-I.beta.), IL-6, IL-18, lymphotactin, myeloperoxidase (MPO), tissue inhibitor of metalloproteinase 1 (TIMP-1), C-reactive protein (CRP), macrophage-derived chemokine (MDC), macrophage inflammatory protein-I .alpha. (MIP-1.alpha.), vWF, and oncostatin.

* * * * *